United States Patent
Wojewoda et al.

(10) Patent No.: US 8,206,214 B2
(45) Date of Patent: Jun. 26, 2012

(54) PLAYER ROSTER SELECTION INTERFACE

(75) Inventors: Lukasz Wojewoda, Santa Monica, CA (US); Shawn G. Robinson, San Jose, CA (US)

(73) Assignee: Yahoo! Inc., Sunnyvale, CA (US)

( * ) Notice: Subject to any disclaimer, the term of this patent is extended or adjusted under 35 U.S.C. 154(b) by 374 days.

(21) Appl. No.: 11/406,663

(22) Filed: Apr. 18, 2006

(65) Prior Publication Data

US 2007/0243917 A1  Oct. 18, 2007

(51) Int. Cl.
A63F 9/24  (2006.01)
(52) U.S. Cl. .......................... 463/29; 463/42
(58) Field of Classification Search ............ 463/20, 463/1–5
See application file for complete search history.

(56) References Cited

U.S. PATENT DOCUMENTS

| | | | | |
|---|---|---|---|---|
| 5,636,920 | A * | 6/1997 | Shur et al. | 700/91 |
| 5,971,854 | A * | 10/1999 | Pearson et al. | 463/41 |
| 6,041,266 | A * | 3/2000 | Nickerson | 700/92 |
| 6,193,610 | B1 * | 2/2001 | Junkin | 463/40 |
| 6,371,855 | B1 | 4/2002 | Gavriloff | |
| 6,656,042 | B2 | 12/2003 | Reiss et al. | |
| D491,956 | S | 6/2004 | Ombao et al. | |
| D499,740 | S | 12/2004 | Ombao et al. | |
| D510,362 | S | 10/2005 | Minagawa et al. | |
| D538,295 | S | 3/2007 | Noviello et al. | |
| D538,815 | S | 3/2007 | Noviello et al. | |
| D538,816 | S | 3/2007 | Noviello et al. | |
| D538,817 | S | 3/2007 | Noviello et al. | |
| D538,818 | S | 3/2007 | Noviello et al. | |
| D549,717 | S | 8/2007 | Noviello et al. | |
| D550,233 | S | 9/2007 | Vigesaa | |
| D550,241 | S | 9/2007 | Viegers et al. | |
| D551,675 | S | 9/2007 | Noviello et al. | |
| D554,653 | S | 11/2007 | Noviello et al. | |
| D557,702 | S | 12/2007 | Viegers et al. | |
| D558,213 | S | 12/2007 | Noviello et al. | |
| D559,259 | S | 1/2008 | Noviello et al. | |
| D559,260 | S | 1/2008 | Noviello et al. | |
| D569,869 | S | 5/2008 | Chotai et al. | |
| D571,373 | S | 6/2008 | Loehr et al. | |
| D572,717 | S | 7/2008 | Loehr et al. | |
| D579,943 | S | 11/2008 | Clark et al. | |
| D594,012 | S | 6/2009 | Ng et al. | |
| D594,464 | S | 6/2009 | Ng et al. | |
| 7,618,312 | B1 | 11/2009 | Kasten | |
| 2001/0034734 | A1 * | 10/2001 | Whitley et al. | 707/104.1 |
| 2002/0040253 | A1 * | 4/2002 | McNally et al. | 700/91 |
| 2002/0107073 | A1 | 8/2002 | Binney | |

(Continued)

OTHER PUBLICATIONS

Turbostats.com website Archive page dated Mar. 6, 2001.*

(Continued)

*Primary Examiner* — Masud Ahmed
(74) *Attorney, Agent, or Firm* — James J. DeCarlo; Greenberg Traurig, LLP

(57) ABSTRACT

A player roster interface is described. In one example, player roster interface logic includes display logic operable to display a playing region (which may include a graphical representation of a playing field associated with a sport) and player logic operable to display a plurality of players, wherein at least a portion of the players may be displayed within the playing region. The interface logic further includes selection logic operable to determine a player roster based on the position of the players relative to the playing region. Such an interface may allow a user to select and view a player roster (e.g., for a fantasy sports team) by positioning players within the playing region.

18 Claims, 5 Drawing Sheets

U.S. PATENT DOCUMENTS

| | | | |
|---|---|---|---|
| 2005/0164792 A1 | 7/2005 | Wilcock | |
| 2005/0228780 A1 | 10/2005 | Diab et al. | |
| 2006/0183548 A1* | 8/2006 | Morris et al. | 463/42 |
| 2006/0217198 A1* | 9/2006 | Johnson | 463/40 |
| 2006/0258421 A1 | 11/2006 | Nicholas et al. | |
| 2007/0021165 A1 | 1/2007 | Ma et al. | |
| 2007/0060325 A1* | 3/2007 | Gradek | 463/29 |
| 2007/0185599 A1 | 8/2007 | Robinson et al. | |
| 2007/0203591 A1 | 8/2007 | Bowerman et al. | |
| 2007/0243918 A1 | 10/2007 | Wojewoda et al. | |
| 2008/0026804 A1 | 1/2008 | Baray et al. | |
| 2008/0033840 A1 | 2/2008 | Updendran et al. | |
| 2008/0096664 A1 | 4/2008 | Baray et al. | |
| 2008/0102911 A1 | 5/2008 | Campbell et al. | |
| 2008/0147575 A1 | 6/2008 | Roy | |
| 2008/0153589 A1 | 6/2008 | Baray et al. | |
| 2008/0155436 A1 | 6/2008 | Hirano et al. | |
| 2008/0161113 A1 | 7/2008 | Hansen et al. | |
| 2009/0156311 A1 | 6/2009 | Ng et al. | |
| 2009/0156312 A1 | 6/2009 | Ng et al. | |

OTHER PUBLICATIONS

Archive date page For Turbostats.com shown date of Mar. 6, 2001.*

Anonymous. (2000). Y! Sports Screen Shot of Fantasy Baseball Home )Page, one page.

Anonymous. (Sep. 29, 2004). Y! Sports (ID#101) GMC Fantasy Baseball Plus Screen Shot, one page.

Non-Final Office Action for U.S. Appl. No. 11/959,378, mailed Jan. 4, 2011.

Non-Final Office Action for U.S. Appl. No. 11/603,496, mailed Feb. 1, 2011.

Waybackmachine. (Jun. 11, 2009) Internet Archive WayBack Machine, <http://web.archive.org/web*/http://turbostats.com/baseline.htm.>, last visited on Jun. 11, 2009.

Official Action issued in connection with U.S. Appl. No. 11/603,496 mailed Nov. 26, 2010.

Official Action issued in connection with U.S. Appl. No. 11/603,496 mailed Aug. 6, 2010.

Official Action issued in connection with U.S. Appl. No. 11/603,496 mailed Jun. 16, 2010.

Official Action issued in connection with U.S. Appl. No. 11/603,496 mailed Dec. 23, 2009.

* cited by examiner

PLAYER ROSTER SELECTION INTERFACE

BACKGROUND

1. Field

The present invention relates generally to sports, and more particularly, to the selection of player rosters for sports and fantasy sports games.

2. Related Art

Generally speaking, fantasy sports are virtual games where users, referred to often as owners, build a collection or "team" of players that compete against teams created by other users. The teams typically include players from a professional sport (e.g., football, soccer, baseball, basketball, hockey, etc.). The players accumulate points within the fantasy sport game based on their individual (and sometimes team) statistics, i.e., statistics from the actual player performances over time. For example, typically, a predetermined or agreed upon model is used to associate actual statistics of individual players into points. Teams thereby compete based on the number of points accumulated over a given period. The period may be based on a weekly schedule, number of games, season, etc.

A fantasy football league, for example, may include several teams of players selected by users. The players may be selected based on a "draft" or other means whereby the users select players generally based on their expected performance. Typically, a team must draft a number of players for each position such as quarterback, running back, wide receiver, kicker, and so on.

Additionally, in some variations of fantasy sports the user has the option of substituting players in and out of a starting line-up or roster. For example, some of an owner's team may "start", i.e., are used to accumulate points for a particular cycle (e.g., on a given day, week, or game(s)) while other players are "benched", i.e., are unused or left out of the point accumulations for the team. Continuing with the fantasy football example, an owner may have two quarterbacks that may be used in a given cycle; however, typically only one may "start" per cycle. The owner therefore chooses which player to start and which to bench.

SUMMARY

Described herein are system and methods for a sports player roster selection interface. In one aspect, player roster interface logic is described, the player roster interface logic includes display logic operable to display a playing region (which may include, e.g., a graphical representation of a playing field, a table, or a window) and player logic operable to display a plurality of players (e.g., small/thumbnail images of the players), wherein at least a portion of the players may be displayed within the playing region. The interface further includes selection logic operable to determine a player roster based on the position of the players relative to the playing region. Such an interface may allow a user to select and view a player roster (e.g., for a fantasy sports team) within the playing region.

The interface may further include logic operable to display players outside of the playing region (e.g., and in a bench region to indicate players not on the roster). In one example, players may be moved to and from the playing region (as well as within the playing region) in response to drag-and-drop operations. In other examples, players may be selected for inclusion within the playing region in response to a selection from a drop-down menu. In some examples, the interface may further calculate points (e.g., based on a fantasy sports league model) for the selected roster.

In another aspect, a method for selecting a player roster (e.g., for a sports or fantasy sports team) is provided. In one example, the method includes displaying a playing region (including a graphical representation of a playing field, for example), displaying a plurality of players within the playing region, and determining a player roster based on the position of the players relative to the playing region. The players may be displayed and positioned within the playing region in response to user input, e.g., in response to drop-and-drag operations, drop-down menu selections, or the like.

According to another aspect, a computer program product comprising program code for selecting a roster (e.g., for a sports or fantasy sports team) is provided. The computer program product may include program code operable to display a playing region and a plurality of players, wherein at least a portion of the players may be positioned within the playing region. The program code may further be operable to determine a player roster based on the position of the players relative to the playing region.

The various aspects and examples of the present inventions are better understood upon consideration of the detailed description below in conjunction with the accompanying drawings and claims.

DETAILED DESCRIPTION

The following description is presented to enable a person of ordinary skill in the art to make and use the invention. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the invention. Thus, the present invention is not intended to be limited to the examples described herein and shown, but is to be accorded the scope consistent with the claims.

According to one example described herein, a user interface is provided for selecting a player roster within a fantasy sports context. In one example, the interface displays a playing region and a bench region, whereby a user may position players within the playing region to indicate their status on the roster. In one example, the interface further displays a graphical representation of a playing field of the particular sport. The "playing field" or "field" may include, e.g., a drawn outline or image of at least a portion of a playing field, court, arena, or the like associated with a sport such as soccer, football, baseball, basketball, hockey, and the like. Players for a user's team may be viewed (e.g., via an image or text) and positioned within the playing region and/or playing field to designate a starting roster.

Further, in one example the position of the players within the playing region is associated with the particular position.

For example, columns for different positions may be included where players are positioned accordingly; in other examples where a playing field is displayed, different positions may be positioned within the playing region according to the playing field. The playing field may further include a "benched" region, e.g., out of bounds or near the sideline of the playing field, where players that are not starting may be positioned and viewed. In one example, a user may "drag-and-drop" players, e.g., from a benched region to the playing region or field to indicate the starting roster. In other examples, a user may select players to start within the playing field from one or more menus, e.g., drop-down menus.

It will be appreciated that the players in the fantasy sports league can be professional athletes, semi-professional athletes, college athletes, high school athletes, recreational league players, little league players, and the like. Further, the interface may be used in non-fantasy sports related applications, e.g., to select a starting roster for a professional or recreational team.

Figure 1:
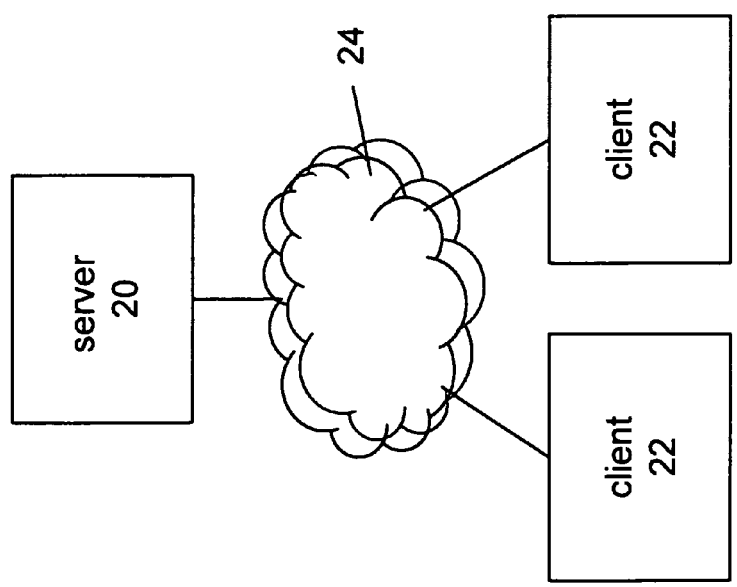
FIG. 1 illustrates an exemplary environment in which certain aspects and examples of the systems and methods described may be carried out.

FIG. 1 illustrates a block diagram of an exemplary environment in which certain aspects of the user interface and methods described may operate. Generally, one or more clients 22 may access a server 20. The server 20 and clients 22 may include any one of various types of computer devices, having, e.g., a processing unit, a memory (including a permanent storage device), and a communication interface, as well as other conventional computer components (e.g., input device, such as a keyboard and mouse, output device, such as display). For example, client computer 22 may include a desktop computer, laptop computer, mobile device such as a mobile phone, web-enabled phone, smart phone, and the like.

Clients 22 and server 20 may communicate, e.g., via suitable communication interfaces via a network 24, such as the Internet. Clients 22 and server 20 may communicate, in part or in whole, via wireless or hardwired communications, such as Ethernet, IEEE 802.11b wireless, or the like. Additionally, communication between clients 22 and server 20 may include various servers such as a mail server, mobile server, and the like.

The server 20 includes logic or is programmed to format data, accessed from local or remote databases or other sources of data, for presentation to users of clients 22, preferably in the format discussed in detail below. The server 20 may utilize various Web data interface techniques such as Common Gateway Interface (CGI) protocol and associated applications (or "scripts"), Java® "servlets", i.e., Java® applications running on the Web server, or the like to present information and receive input from clients 22. The server 20, although described herein in the singular, may actually comprise plural computers, devices, backends, and the like, communicating (wired and/or wireless) and cooperating to perform some or all of the functions described herein.

Figure 2A:
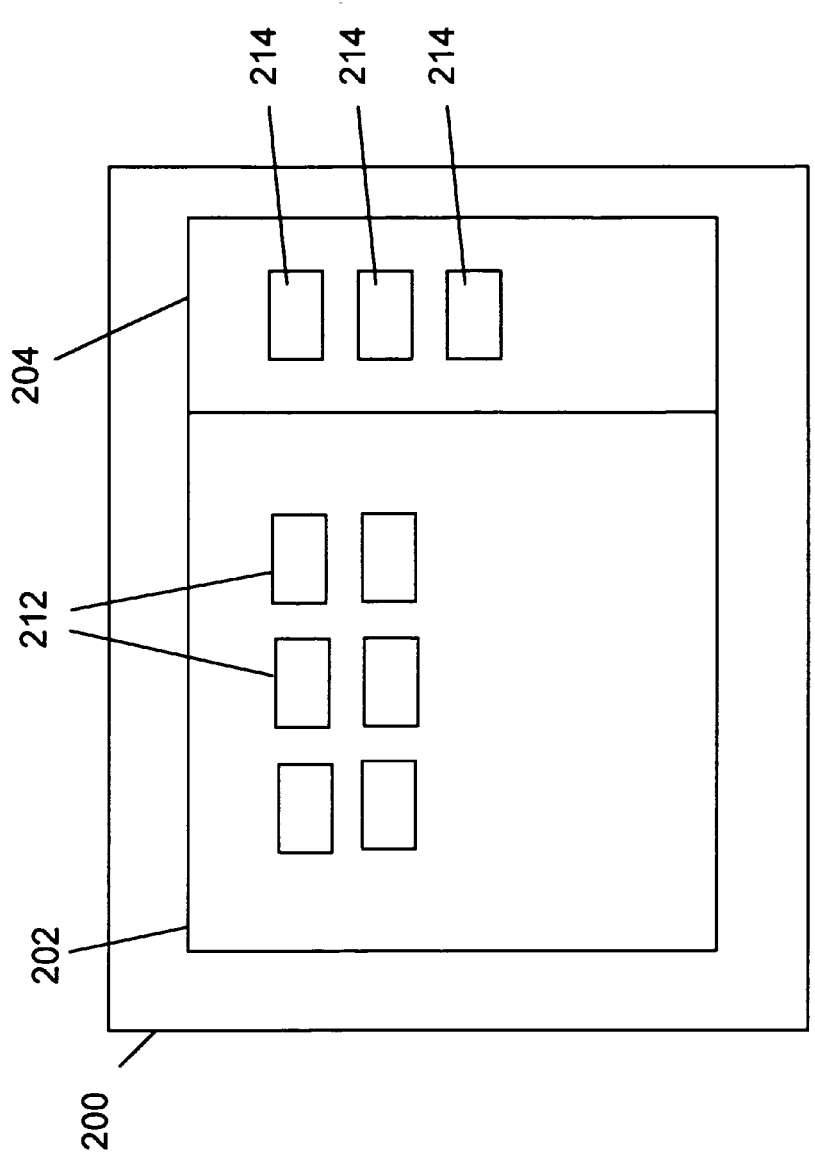
FIGS. 2A and 2B illustrate exemplary interfaces for selecting player rosters.

FIG. 2A illustrates an exemplary player roster interface 200 for selecting a player roster. The player roster interface 200 may be stored as an application in any computer system; for example, the player roster interface 200 may operate on one or more computer devices, including stand alone computers, server computers connected to client computers over a network, or the like. In one particular example, the player roster interface 200 may run as an application on a server computer or computers (see, e.g., server 20 of FIG. 1). Users may access and input selections via client computers through a Web browser or the like. In other examples, the player roster interface 200 may run as an application on a stand-alone computer. Of course, various other methods and systems for displaying and accessing the player roster interface 200 are possible.

The player roster interface 200 may be displayed, for example, in one or more windows on a computer screen, or in a Web browser. Player roster interface 200 may have associated therewith computer program code in HyperText Markup Language (HTML), Dynamic HTML, JavaScript®, Java®, combinations thereof, or any other form of computer-executable code, for causing user interface elements, such as those shown in FIGS. 2A-4, to be displayed to a user and to accept user interactions.

In one example, the process is initiated by a user entering into his or her browser the Uniform Resource Locator (URL) of a server Web site. In response to receipt of this communication from a participant's browser, logic or software operating at the server controls the server to send the browser information associated with the interface, e.g., an HTML document or Dynamic HTML document, having features and functionality as discussed herein. An interactive session may follow, whereby the user may select player rosters as described. Additionally, depending on the implementation, various log-in and user identification methods and interfaces may be used as will be understood by those of ordinary skill in the art.

Generally, player roster interface 200 includes a playing region 202, where players 212 may be positioned in response to user input to indicate a roster. The player roster interface 200 includes logic for displaying playing region 202, players 212, and for determining or selecting the roster based on the positioning of players 212 within playing region 202. For example, the roster may be determined by the presence of players 212 within playing region 202 (as opposed to bench region 204 or not displayed).

In some examples, player roster interface 200 may further include display logic operable to display a graphical representation (e.g., an outline, image, etc.) of a playing field within playing field region 202, the graphical depiction of the playing field associated with a particular sport. A playing field with playing region 202 may depict various athletic venues, such as a soccer field, football field, hockey field, baseball diamond, basketball court, and so on. Further, the playing region 202 may display an actual image of a playing field, only a portion of a playing field, or a representation of a playing field. For example, playing region 202 may include a green background to indicate grass, a hardwood background to indicate a basketball court, and the like.

Figure 2B:
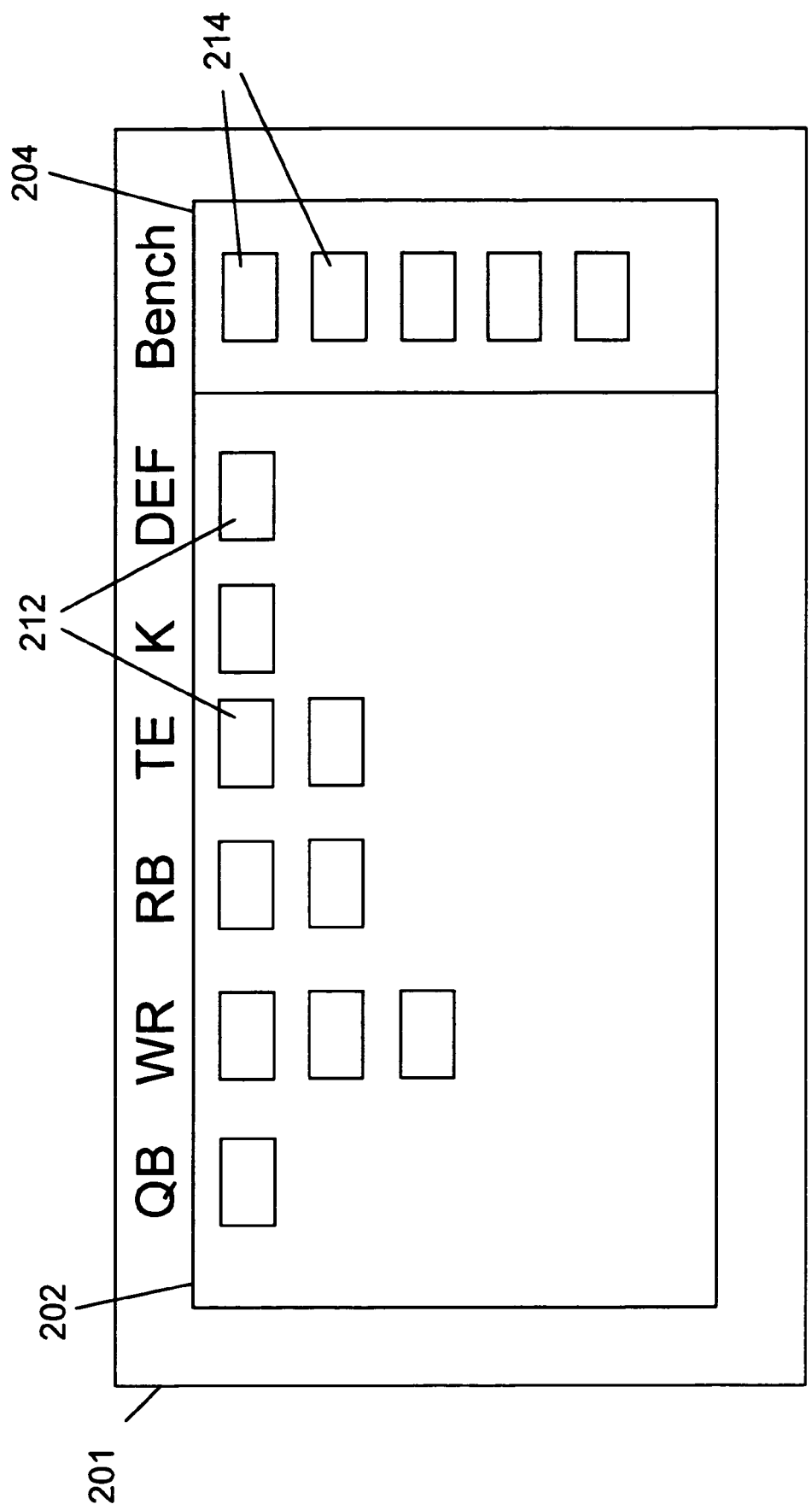

FIG. 2B illustrates another exemplary player roster interface 201, similar to player roster interface 200. In this example, playing region 202 includes areas for particular positions such as "Q" for quarterback, "WR" for wide receiver, and so on. Accordingly, players 212 are positioned within playing region 202 and within appropriate player position areas. Player roster interface 201 may further include logic to prevent or alert a user from adding players to the wrong position, having too many or too few players at a given position, and the like.

With reference to both FIGS. 2A and 2B, the relative position of players 212 and 214 to playing region 202 indicates players selected for the roster. In these examples, players 212 are positioned within playing region 202 to indicate they are included on the roster and players 214 positioned outside of playing region 202 to indicate they are not on the roster. Players 212 and 214 may include an icon, image, text or other discernable indicia associated with the players available to the particular user (e.g., those players on the user's team). Players 212 and 214 may each include an image of the player, text description (e.g., name, number, team, etc.), or combinations thereof. Player roster interface 200 thereby provides a graphical representation of a user's team, and in particular, those players 212 on the starting roster and those players 214 that are benched.

Additionally, in other examples, the position of players 212 within playing region 202 may correspond generally to an actual player position in the field of play (e.g., for hockey positioning the goalie, center, wingers, and defensemen approximately as they might be positioned for a face-off, during a play, etc.). In other examples, players 212 may be positioned in areas (e.g., similar to columns of a table as shown in FIG. 2B) of playing region 202 according to different positions. In other examples, however, the position of players 212 within playing region 202 is not associated with an actual player position and only indicates their status on the roster.

Player roster user interfaces 200 and 201 further include a bench region 204, where players 214 are positioned. Players 214 may also include an icon, hyperlink, image, text or other discernable indicia associated with the player's identity. The manner in which players 212 and 214 are displayed may be identical or different based on whether they are within the playing region 202 or bench region 204. In other examples, players 214 could be positioned within a common window and shown outside of the playing region 202, or at least in a position that would indicate players 214 are not on the starting roster. In another example, players 214 could be positioned within playing region 202, but de-emphasized in some way, for example, shadowed, reduced in size, or the like to indicate the player status to a user.

In one example, players 212 and 214 correspond to players of a particular user's team, and are therefore available to a user for selecting their team roster. Initially, all players may be in bench region 204 and available for selection by a user to the roster. In other examples, a default starting roster may be used to populate playing region 202, e.g., based on previous starting rosters, player rankings, individual player statistics, past point accumulations, and the like. Alternatively, a third region could exist where the player's status is neither on nor off of the roster.

Players 212 and 214 may be moved within player roster interface 200 in response to drag-and-drop operations. For example, a user may select and drag players 212 and 214 to and from playing region 202 and bench region 204. In particular, a user may make a selection of one of the players 212 or 214 by moving a cursor over the player to select and "drag" (e.g., moving the cursor while clicking and holding a mouse button or the like) the player to the playing region 202 or bench region 204. In other examples, a user may select a player and enter a command (e.g., via a keyboard, mouse, or other input device) to move a player from playing region 202 to bench region 204 and vice-versa.

In still another example, playing region 202 may include a plurality of drop-down menus positioned, for example, according to the particular position over playing region 202. A user may select the drop-down menu to select from available players at the particular position to be displayed within playing region 202. In one example, bench region 204 may be omitted in such an example; however, in other examples, bench region 204 may display those players which have not been selected to be displayed within playing region 202.

Figure 3:
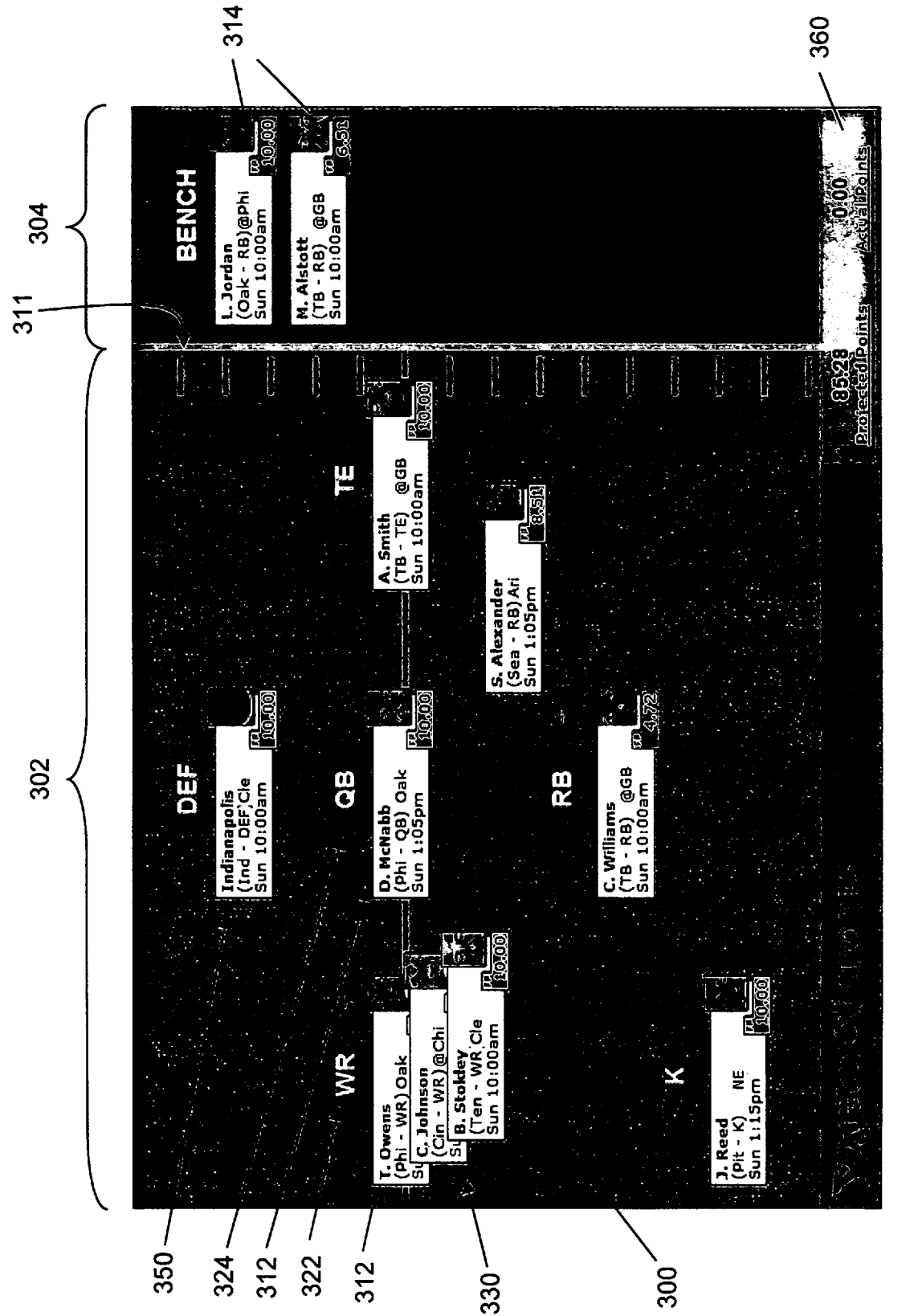
FIG. 3 illustrates another exemplary interface for selecting a player roster.

FIG. 3 illustrates an exemplary user interface 300 according to one illustrative example. In this example, user interface 300 displays a playing region 302 and a bench region 304, where the bench region 304 is demarcated by a side-line 311. Similar to the example described above, players 312 are shown within playing region 302 to indicate they are on the starting roster, and players 314 are illustrated in bench region 304 (in this example, outside of the side-line 311) to illustrate they are not on the starting roster. Further, playing region 302 includes a graphical representation of a playing field associated with the particular sport, in this example, a portion of a football field.

In this example, players 312 and 314 include an image of the player, the name of the player name, and other statistics, such as their team, position, upcoming opponent, and date/time of one or more upcoming games. Various other player information, including, e.g., current or past statistics, may also be included. Additionally, in this example, each player 312 is positioned within playing region 302 according to their particular position (e.g., wide receiver "WR", quarterback "QB", and so on) as indicated by 322 and 324. Some positions may include more than one starter; accordingly, in this example, multiple players 312 may be positioned at the "WR" position as indicated by 330.

User interface 300 may further include logic operable to prevent a user from adding more than a particular number of players to a position and/or provide an indication that more players need to be added to a position (e.g., by displaying a blank or shadowed image to indicate another player is needed). Thus, a user may visually see if the roster is valid, and may reduce or prevent the user from submitting an invalid roster.

Additionally, user interface 300 may include a defensive team selection indicated by 350. For example, in some fantasy sports games, a user selects a defensive team as opposed to individual defensive players.

User interface 300 further includes logic operable to calculate points based on players 312 selected for the roster (e.g., by being positioned with playing region 302) and display the points at 360. Points may be accumulated in a variety of ways depending on the particular fantasy sports league, configuration, etc., and are typically associated with each of the individual player's statistics. In this example, user interface 300 displays projected points of players 312 in playing region 302, which may be based on average performances of players 312 in previous games, seasons, career, versus upcoming opponent(s), and the like, or combinations thereof. Additionally, the actual points may be displayed, for example, after a particular game or cycle has concluded. The points at 360 may be updated in real time as a user moves a player to or from playing region 302, thereby allowing a user to quickly view projected points for their selected roster.

Additionally, in some examples, an opposing fantasy sports team may be displayed within playing region 302. For example, in some versions of fantasy sports games, a user's team competes for points against another user's team (e.g., in the same fantasy league). Thus, in one example, the roster or team of an opponent may also be displayed in playing region 302 or otherwise displayed to the user.

Figure 4:
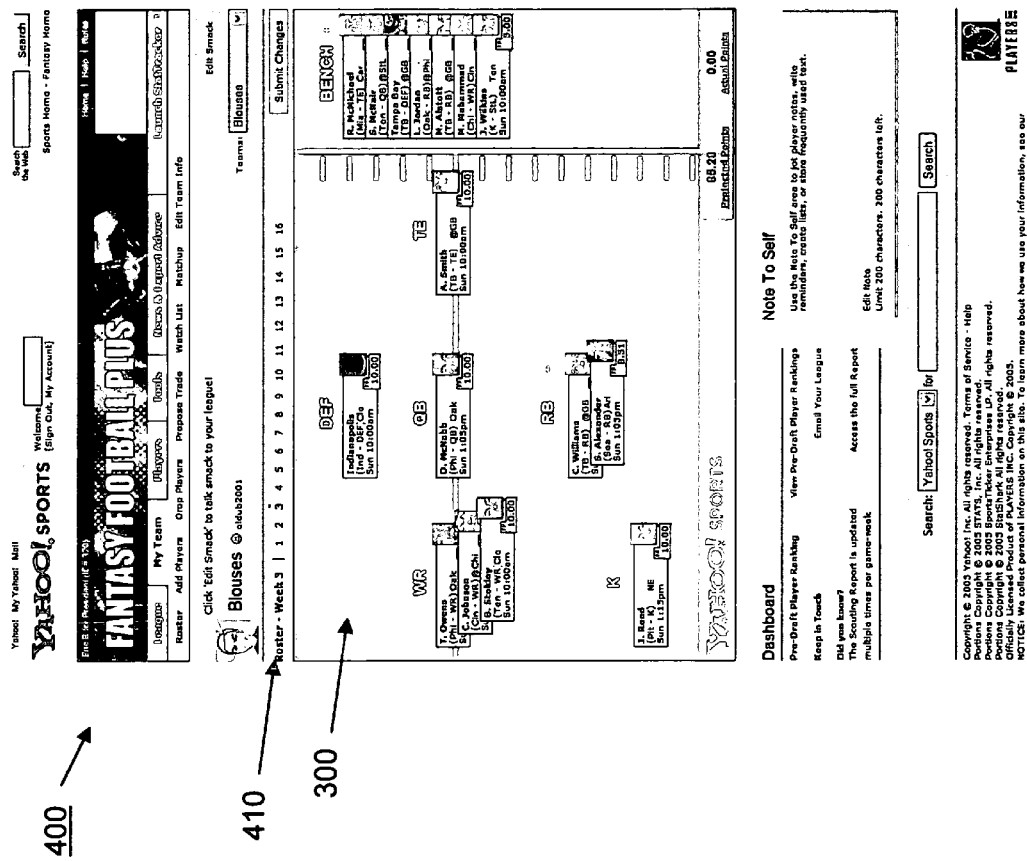
FIG. 4 illustrate an exemplary window or interface including an interface for selecting a player roster.

FIG. 4 illustrates user interface 300, similar to that illustrated in FIG. 3, included within a page or window 400 of a web browser. In this particular example, user interface 300 is illustrated as part of a Yahoo!® SPORTS page; however, a similar or identical user interface may be included with any webpage, as a stand alone browser application window, and the like. As illustrated, window 400 may include various user specific information, such as the particular team the user is associated with, player rankings, and the like.

In this example, interface 300 further includes a roster cycle feature 410 to view rosters for varying cycles. For example, during a football season (which typically has 17 weeks during its regular seasons) a user may select a given week to view and select their roster for that week. A user may also view their previous rosters and accumulated points.

Figure 5:
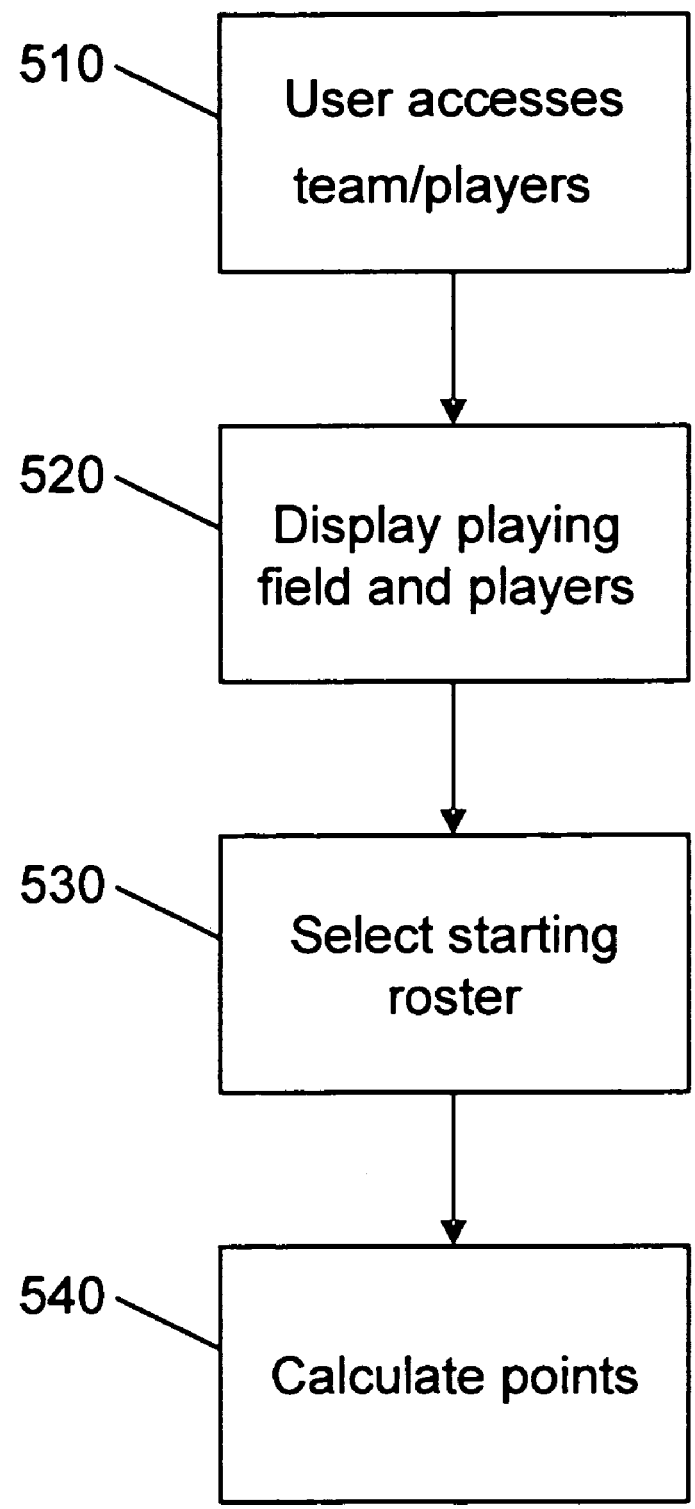
FIG. 5 illustrates an exemplary method for selecting a player roster.

FIG. 5 illustrates an exemplary method for selecting a starting roster for a sports or fantasy sports team. Initially, a user accesses a team including a plurality of players at 510. The user may access the team and players by logging into an appropriate application or Website, opening a window or program, etc., associated with a roster selection interface. A user may be required to initially select players for their team depending on the particular fantasy sports league etc., and the player roster interface may thereafter retrieve the team and player data in response to an identification of the user, e.g., upon log-in of the user.

The method may further include displaying a playing field region, which may comprise a graphical representation of a playing field, and the players of the user's team at 520. For example, an interface may include logic operable to display a playing field associated with the particular sport and the players associated with the user.

The method may further include selecting a roster based on input from the user at 530. For example, the roster is selected based on the positioning of the players by the user relative to the displayed playing field region and/or graphical representation of the playing field. As described, players positioned within or over the playing field region may be determined as part of the starting roster. Players positioned outside of the playing field or in a designated region are determined as not part of the starting roster. Accordingly, the interface may include selection logic operable to determine the roster based on the position of the players with respect to the playing field. The selection may then be stored.

Additionally, the method may include calculating points based on the selected roster at 540. The points may be projected points based on past statistics of the players or points accumulated in the last playing cycle as described.

The various aspects and examples may be implemented in any suitable form including hardware, software, firmware or any combination of these, and, in particular, in program code and associated hardware. Different aspects of the invention may be implemented at least partly as computer software or firmware running on one or more data processors. The elements and components of an embodiment of the invention may be physically, functionally and logically implemented in any suitable way. Indeed the functionality may be implemented in a single unit, in a plurality of units or as part of other functional units. As such, the invention may be implemented in a single unit or may be physically and functionally distributed between different units and processors.

Although the present invention has been described in connection with some examples, it is not intended to be limited to the specific form set forth herein. Rather, the scope of the present invention is limited only by the claims. Additionally, although a feature may appear to be described in connection with a particular embodiment, one skilled in the art would recognize that various features of the described embodiments may be combined in accordance with the invention. Moreover, aspects of the invention describe in connection with an embodiment may stand alone as an invention.

Moreover, it will be appreciated that various modifications and alterations may be made by those skilled in the art without departing from the spirit and scope of the invention. The invention is not to be limited by the foregoing illustrative details, but is to be defined according to the claims.

What is claimed is:

1. A computing device comprising:
   a processor;
   storage media for tangibly storing thereon program logic comprising:
   display logic executing on the computing device processor for displaying, on a display of the computing device, a playing region and a region outside of the playing region, the playing region comprising a graphical representation of a playing field;
   player logic executing on the computing device processor for displaying, on the display of the computing device, a plurality of players, wherein at least a portion of the players may be positioned and displayed in a first display manner within the playing region, and at least a portion of the players may be positioned and displayed in a second display manner different than the first display manner within the region outside of the playing region, and wherein the plurality of players is associated with a fantasy sports team of an identified user;
   moving logic executing on the computing device processor for selectively moving a portion of the plurality of players from the playing region to the region outside of the playing region and vice versa; and
   selection logic executing on the computing device processor for determining a player roster based on the position of the players relative to the playing region, where the selection logic excludes players positioned outside of the playing region from the player roster.

2. The computing device of claim 1, wherein the display logic further comprises display logic for displaying a graphical representation of a playing field in the playing region.

3. The computing device of claim 1, further comprising selection logic for including players positioned within the playing region on the player roster.

4. The computing device of claim 1, wherein the storage media further comprises logic for positioning a player within the playing region in response to a user drag-and-drop operation.

5. The computing device of claim 1, wherein the storage media further comprises logic for displaying a player in response to user selection of a player from a drop-down menu.

6. The computing device of claim 1, wherein the storage media further comprises logic operable to calculate points based on the players determined to be on the player roster.

7. A method comprising:
   displaying, on a display of a computing device, a playing region and a region outside of the playing region, the playing region comprising a graphical representation of a playing field;
   displaying, on the display of the computing device, a plurality of players in response to user input, wherein at least a portion of the players may be positioned and displayed in a first display manner within the playing region, and at least a portion of the players may be positioned and displayed in a second display manner different than the first display manner in the region outside of the playing region, and wherein the plurality of players is associated with fantasy sports team of an identified user;
   selectively moving, by the computing device, a portion of the plurality of players from the playing region to the region outside of the playing region and vice versa; and
   determining, by the computing device, a player roster based on the position of the players relative to the playing region, wherein the determining of a player roster further comprises excluding players positioned in the region outside of the playing region from the player roster.

8. The method of claim 7, wherein the playing region includes a graphical representation of a playing field.

9. The method of claim 7, further comprising moving the position of a player relative to the playing region in response to a drag-and-drop operation.

10. The method of claim 7, further comprising selecting a player to be displayed within the playing region in response to a selection of the player from a drop-down menu.

11. The method of claim 7, further comprising determining a player roster based on the displayed players within the playing region.

12. The method of claim 7, further comprising calculating points based on the players within the playing region.

13. A computer readable storage medium comprising program code tangibly stored thereon for selecting a player roster, the computer readable storage medium comprising program code for:
   displaying, on a display of a computing device, a playing region and a region outside of the playing region, the playing region comprising a graphical representation of a playing field;
   displaying, on the display of the computing device, a plurality of players, wherein at least a portion of the players may be positioned and displayed in a first display manner within the playing region, and at least a portion of the players may be positioned and displayed in a second display manner different than the first display manner in the region outside of the playing region, and wherein the plurality of players is associated with fantasy sports team of an identified user;
   selectively moving, on the display of the computing device, a portion of the plurality of players from the playing region to the region outside of the playing region and vice versa; and
   determining, by the computing device, a player roster based on the position of the players relative to the playing region, wherein the determining further comprises excluding players positioned in the region outside of the playing region from the player roster.

14. The computer readable storage medium of claim 13, further comprising program code operable to display a graphical representation of a playing field in the playing region.

15. The computer readable storage medium of claim 13, further comprising program code operable to include players positioned within the playing region on the player roster.

16. The computer readable storage medium of claim 13, further comprising program code operable to position a player within the playing region in response to a drag-and-drop operation.

17. The computer readable storage medium of claim 13, further comprising program code operable to display a player in response to a user selection of the player from a drop-down menu.

18. The computer readable storage medium of claim 13, further comprising program code operable to calculate points based on the players on the player roster.

* * * * *